United States Patent [19]

Deller et al.

[11] Patent Number: 5,132,452
[45] Date of Patent: Jul. 21, 1992

[54] METHOD FOR PREPARATION OF GLUCONIC ACID BY CATALYTIC OXIDATION OF GLUCOSE

[75] Inventors: Klaus Deller, Hainburg; Helmfried Krause, Rodenbach; Erik Peldszus, Hasselroth; Bertrand Despeyroux, Hanau, all of Fed. Rep. of Germany

[73] Assignee: Degussa Aktiengesellschaft, Frankfurt am Main, Fed. Rep. of Germany

[21] Appl. No.: 626,422

[22] Filed: Dec. 14, 1990

Related U.S. Application Data

[63] Continuation of Ser. No. 374,875, Jul. 3, 1989, abandoned.

[30] Foreign Application Priority Data

Jul. 9, 1988 [DE] Fed. Rep. of Germany ....... 3823301

[51] Int. Cl.$^5$ .................... C07C 51/235; C07C 59/105
[52] U.S. Cl. .................................... 562/531; 502/185; 502/325
[58] Field of Search .................. 562/531; 502/325, 185

[56] References Cited

U.S. PATENT DOCUMENTS

4,843,173  6/1989  Saito .................................. 562/531

FOREIGN PATENT DOCUMENTS

| 1142959 | 3/1983  | Canada ............................... 562/531 |
| 0005779 | 12/1979 | European Pat. Off. . |
| 0142725 | 5/1985  | European Pat. Off. . |
| 0151498 | 8/1985  | European Pat. Off. . |
| 2903388 | 9/1979  | Fed. Rep. of Germany ...... 562/531 |
| 2836327 | 2/1980  | Fed. Rep. of Germany . |

Primary Examiner—Vivian Garner
Attorney, Agent, or Firm—Beveridge, DeGrandi & Weilacher

[57] ABSTRACT

A process for making gluconic acid and its alkali metal salts by oxidizing glucose with oxygen or oxygen containing gas in an aqueous alkaline solution in the presence of an activated charcoal supported catalyst containing a platinum group metal component, e.g. platinum and palladium and bismuth wherein the platinum, palladium and bismuth are simultaneously deposited on the charcoal support.

18 Claims, No Drawings

METHOD FOR PREPARATION OF GLUCONIC ACID BY CATALYTIC OXIDATION OF GLUCOSE

This application is a continuation of U.S. patent application Ser. No. 07/374,875, filed Jul. 3, 1989 now abandoned.

INTRODUCTION AND BACKGROUND

The present invention relates to a process for making gluconic acid or its alkali metal salts by oxidizing glucose with oxygen or with an oxygen containing gas in an aqueous alkaline solution in the presence of a supported catalyst containing a platinum group metal and bismuth.

Large-scale fermentation is one known method for making gluconic acid; another method is catalytic and is based on glucose which is subjected to oxidation with an oxygen containing gas in an aqueous alkaline solution in the presence of a heterogeneous catalyst.

A representative procedure is described in the European patent disclosure 0 142 725 which employed a palladium-bismuth catalyst supported on activated charcoal. This method leads to a glucose conversion of 99.8% and a yield of gluconic acid in the form of its sodium salt of 99.5%. The selectivity for formation of gluconic acid sodium salt is stated being 99.7%. The proportion of the fructose isomerization product is stated as being reduced to 0.1%. However, the catalytic activity value is no higher than 1,450 g of product per gram of Pd used per hour of reaction time. Because of the accuracy of measurement of ±2% of the HPLC method or ion-chromatography, the above data concerning the selectivity and the quantity of the fructose isomerization product are questionable.

The German OLS 28 36 327 describes the oxidation of aryl glycols by means of an oxygen containing gas in an aqueous, alkaline medium into the corresponding alphaketocarboxylic acid esters using a platinum-bismuth catalyst on an activated charcoal support.

The European Patent 0 005 779 describes the oxidation of alpha-hydroxyaryl acetic acids into arylglyoxyl acids using an oxygen containing gas in an aqueous, alkaline medium with platinum catalysts in the simultaneous presence of lead and/or bismuth or their compounds. A similar procedure is disclosed in Japanese Kokai Tokkyo Koho JP 56/158733 A 2.

Lastly, the European patent disclosure 0 151 498 discloses the preparation of alpha-ketogluconic acid from glucose with a platinum-bismuth catalyst on activated charcoal, however, the weight ratio of catalyst to glucose is 1.17:1.

In all known systems of reaction employing a platinum-bismuth catalyst on activated charcoal therefore the alpha-hydroxy group is oxidized together with an alcohol group, an aldehyde group or a carbonyl group.

Now it has been found that glucose can be made to react with oxygen in an alkaline medium to form gluconic acid in a selective manner and at a much higher rate of reaction than that of the European patent disclosure 0 142 725, provided that the reaction is carried out on a selected supported catalyst. The latter contains platinum, palladium and bismuth and uses activated charcoal as the support. When employing this catalyst, it is possible to use a quantity of catalyst which is so lowered relative to the amount proposed in the European patent disclosure 0 151 498 that at most a weight ratio of catalyst to glucose of 0.2:1 is required.

SUMMARY OF THE INVENTION

Accordingly, it is an object of the present invention to provide a process for preparing gluconic acid and alkali metal salts thereof by oxidizing glucose with oxygen or with an oxygen containing gas, such as air, in an aqueous, alkaline solution, in the presence of a supported catalyst containing bismuth and a metal selected from the platinum group of noble metal. The process is carried out at reaction temperatures of 20°-80° C. and at an alkaline pH value, i.e. 8.0-11, maintained by continuous addition of alkaline material, such as alkali metal hydroxide, until optimal conversion determined by interim analysis is achieved. A catalytic amount of the catalyst is used in carrying out the reaction. In a more detailed aspect, the weight ratio of this supported catalyst to the glucose is a maximum 0.2. Platinum, palladium and bismuth together constitute the active phase of the catalyst which is deposited on activated charcoal acting as the support and containing from 0.1 to 10% by weight of the precious-metal component containing the platinum and palladium and from 0.01 to 20% by weight of bismuth. A weight ratio of platinum to palladium of 1:99 to 70:30 is used, preferably 15:85 to 50:50 and most preferably 15:85 to 25:75. Following separation of the catalyst from the reaction mixture, the alkali metal gluconate formed thereby can be converted into the free acid.

The catalyst can be produced by impregnating or coating the support with salts, oxides or hydroxides of the said metals of the platinum noble metal group and of the bismuth, followed by reduction.

The following compounds can be used to introduce the metals of the platinum group into the catalyst, namely, platinum compounds such as $H_2PtCl_6$, $H_2PtCl_4$, platinum nitrate, or palladium compounds such as $PdCl_2$, $H_2PdCl_4$ or palladium nitrate in the form of solutions, or oxide compounds such as platinum oxide hydrates, $PdO$ or $Pd(OH)_2$ in the form of suspensions in conventional suspending agents.

Soluble and insoluble bismuth compounds such as bismuth trichloride, bismuth oxychloride, bismuth hydroxy nitrate and bismuth trioxide may be employed to introduce the bismuth in the catalyst.

As may be seen from the foregoing many well known platinum group metal compounds and bismuth compounds can be used for purposes of the invention and any suitable ones may be selected for purposes of this invention.

When preparing the catalyst, simultaneous introduction of the compounds of bismuth and of the platinum metal group is preferred.

The above feature of simultaneous introduction represents a difference relative to the known Pd-Bi catalyst on activated charcoal disclosed in the EPO 0 142 725, supra, wherein mandatorily first impregnation must be carried out with bismuth and upon a substantial interval of exposure only then may the impregnation with precious metal be carried out.

Suitable reducing agents to convert compounds of bismuth and of the platinum metal group introduced in the support by impregnation or deposition are well known in the art and include formaldehyde, hydrazine, hydrogen and other conventional reductants. Formaldehyde is preferred.

Compared to the methods of the EPO 0 142 727, which discloses a Pd-Bi catalyst on activated charcoal, the process of the present invention offers substantially higher rates of reaction. The activity values in the amount of more than 4,000 g of product of gluconic acid per gram of input total precious metal per hour of reaction represent the achievable optimum in accordance with the invention. Activity values are based on amount of product produced by unit of catalyst per unit of time.

In principle, the reaction can be carried out under the pressure of the gaseous oxidation material ranging from normal atmospheric pressure up to 10 bars. Operation at normal atmospheric pressure or at slight excess pressure (3.0 bars) of the oxidizing gas is preferred.

The glucose may be used in the form of 5 to 50%, preferably 10 to 20% by weight aqueous solution.

Preferably, an elevated temperature of reaction; e.g. between 30° and 60° C., is chosen for the reaction. The pH value required to neutralize the formed gluconic acid preferably is between 9 and 11; the pH value is set by constant addition of NaOH to the aqueous solution. As will be apparent to those skilled in the art, other alkali metal compounds can also be used for the neutralization with resulting formation of the corresponding alkali metal salt.

Activated charcoal in powder form is preferred as the support, though granulated material is not excluded. These materials are well known in the art. Activated charcoal with the following properties endows high activity to the catalyst, making possible low glucose isomerization and high glucose yield: BET surface area determined according to DIN 66,131: greater than 500 m$^2$/g; total pore volume: greater than 0.5 ml/g and ash content: less than 5% by weight.

To achieve high activity and selectivity, and illustratively when using a catalyst with 1.0% by weight Pt, 4.0% by weight Pd and 5% by weight of Bi on activated charcoal, advantageously a weight ratio of catalyst to pure glucose also less than 0.1:1 is employed.

The catalyst can be re-used in several batches after it is filtered from the colorless or slightly yellow solution achieved after the optimal rate of conversion has been reached and halt of the reaction.

An essential step within the scope of the present invention is the interruption or halting of the reaction once the optimal rate of conversion has been ascertained by taking several samples in a pilot test. The optimal rate of conversion has been reached when the glucose has been converted, for instance, to the extent of 99% into gluconic acid. It has been found that if the product solution remains in contact with the catalyst beyond that time, undesired byproducts or side products such as glucaric acid, tartaric acid, tartronic acid and oxalic acid will collect which increasingly contaminate the solution of the pure gluconate during the reaction time. Therefore, a pilot batch is used to determine the optimal rate of conversion within the accuracy of measurement using a chromatographic analysis such as HPLC (High Pressure Liquid Chromatography) or ion chromatography, whereupon the optimal time of reaction so ascertained and kept as a standard used for comparison with actual full production runs.

Compared to the state of the art, the present invention offers the advantage of very rapid and highly selective formation of pure gluconic acid from glucose. The activity values obtained thereby are high and can be above 4,000 g of gluconic acid per g of total input precious metal per h of reaction time; that is, they are exceedingly high. It was furthermore unforeseeable that the described procedure would allow rapid and, in addition, highly selective gluconate preparation wherein further oxidations of the prepared gluconic acid to form undesirable byproducts and also undesired isomerization of the glucose are prevented.

Nor was it foreseeable when using platinum or platinum plus palladium in addition to bismuth, that there would be no significant amounts of undesired 2-ketogluconic acid formed in the reaction solution.

Lastly, it was unforeseeable that a synergistic affect can be achieved by using palladium in combination with platinum and bismuth.

DETAILED EMBODIMENTS OF INVENTION

The invention is discussed below in further detail by means of illustrative Examples.

EXAMPLE 1

Preparing the Catalyst 90 g of macroporous (<5 nm), pulverulent activated charcoal with an average particle diameter of 20 μm are suspended in 0.8 liters of distilled water. 5.57 g of $Bi_2O_3$ (corresponding to 5 g Bi) dissolved in 10 ml (conc.) of HCl (hereafter denoted as "bismuth solution") are mixed with 4 g of a 25% by weight aqueous solution of hexachloroplatinic acid (corresponding to 1 g Pt) and with 20 g of a 20% by weight aqueous solution of tetrachloropalladium acid solution corresponding to 4 g Pd and are added to the charcoal suspension.

The mixture is then heated to 80° C. By adding 13 g of NaOH in the form of a 10% by weight aqueous solution, the suspension is made alkaline (pH = 10.0). After agitation for 20 minutes at 80° C., the platinum, palladium and bismuth compound is reduced by adding 6 ml of aqueous formaldehyde solution, (37% by weight). With agitation the suspension is kept for 15 minutes at 80° C. and then is filtered and washed. A Pt/Pd/Bi-activated charcoal catalyst with 1% by weight Pt, 4% by weight Pd and 5% by weight Bi is obtained.

Glucose oxidation 100 ml of an aqueous glucose solution with 16 g glucose (99% by weight, corresponding to $8.80 \times 10^{-2}$ moles) and 0.24 g of the above described catalyst (1.5% by weight catalyst relative to the glucose) are transferred to a 250 ml agitation reactor with gas-agitator, thermometer, alkali metering, pH electrode and oxygen supply. The oxygen is distributed at 56° C. through the gas agitator into the solution.

The reaction takes place at normal atmospheric pressure. Gluconic acid, the product so obtained, is constantly neutralized by dropwise addition of 10% by weight soda solution. The pH of the suspension is 10.0.

Following the reaction times listed in the Table below, samples are taken and the catalyst is filtered off. The filtrate is analyzed by ion chromatography and HPCL. The following values were found:

TABLE I

| Time (minutes) | Amount of material ($10^{-2}$ moles) | | | |
|---|---|---|---|---|
| | 18 | 20 | 25 | 30 |
| glucose | 0.15 | <0.01 | <0.01 | <0.01 |
| gluconic acid | 8.50 | 8.50 | 8.44 | 8.13 |
| fructose | 0.08 | 0.13 | 0.13 | 0.13 |
| glucaric acid | 0.03 | 0.05 | 0.09 | 0.32 |
| tartaric acid | <0.01 | <0.01 | 0.05 | 0.07 |
| tartronic acid | <0.01 | <0.01 | 0.09 | 0.17 |
| oxalic acid | <0.01 | 0.01 | 0.06 | 0.14 |
| conversion (20'): | 100% | | | |
| selectivity (20'): | 98% | | | |

TABLE I-continued

| Time (minutes) | Amount of material ($10^{-2}$ moles) | | | |
|---|---|---|---|---|
| | 18 | 20 | 25 | 30 |
| activity (20'): | 4,200 g of gluconic acid per g of total precious metal per h. | | | |

The catalyst is separated from the reaction solution and the reaction product sodium gluconate is converted by ion exchange into the free acid. The filtered catalyst is then re-used (with the same results).

CONTROL TEST 1

A test is run according to Example 1 of the EPO 0 42 725 on a Pd-Bi/activated charcoal catalyst with 5% by weight Pd and 5% by weight Bi, also prepared according to said EPO document, for glucose oxidation, under the following conditions:

| Temperature: | 50° C. |
|---|---|
| pH: | 9.5 |
| reagents: | 16 g glucose, 99% by weight (8.8 × $10^{-2}$ moles) |
| | 0.24 g catalyst, 1.5% by weight relative to glucose |
| | 10% by weight NaOH (to adjust pH). |

The test is analyzed as described in Example 1. The following values were obtained:

TABLE II

| Time (minutes) | Amount of material ($10^{-2}$ moles) | | | | | |
|---|---|---|---|---|---|---|
| | 10 | 15 | 20 | 25 | 45 | 60 |
| glucose | 7.00 | 5.53 | 4.07 | 3.09 | 0.04 | 0.02 |
| gluconic acid | 1.60 | 3.00 | 4.40 | 5.40 | 8.46 | 8.50 |
| fructose | 0.16 | 0.20 | 0.26 | 0.27 | 0.26 | 0.26 |
| glucaric acid | <0.01 | <0.01 | <0.01 | <0.01 | 0.01 | 0.01 |
| tartaric acid | <0.01 | <0.01 | <0.01 | <0.01 | <0.01 | <0.01 |
| tartronic acid | <0.01 | <0.01 | <0.01 | <0.01 | <0.01 | <0.01 |
| oxalic acid | <0.01 | <0.01 | <0.01 | <0.01 | <0.01 | <0.01 |
| conversion (45'): | 99.5% | | | | | |
| selectivity (45'): | 97% | | | | | |
| activity (45'): | 1,800 g gluconic acid per g of Pd per h. | | | | | |

The above results in Table II for the prior art process show that while the conversion and selectivity values are satisfactory, the activity values are not.

CONTROL TEST 2

The catalyst is prepared as in Example 1 except that a mixture of a 20% by weight tetrachloropalladium acid and bismuth solution is added. A Pd/Bi-activated charcoal catalyst is obtained with 5% by weight Pd and 5% by weight Bi. Glucose oxidation and analysis are as described for Example 1. The following values are obtained:

TABLE III

| Time (minutes) | Amount of material ($10^{-2}$ moles) | | | |
|---|---|---|---|---|
| | 25 | 32 | 35 | 40 |
| glucose | 2.47 | 0.20 | 0.01 | <0.01 |
| gluconic acid | 6.12 | 8.23 | 8.40 | 8.38 |
| fructose | 0.16 | 0.30 | 0.26 | 0.25 |
| glucaric acid | 0.01 | 0.03 | 0.05 | 0.07 |

TABLE III-continued

| Time (minutes) | Amount of material ($10^{-2}$ moles) | | | |
|---|---|---|---|---|
| | 25 | 32 | 35 | 40 |
| tartaric acid | <0.01 | 0.01 | 0.01 | 0.01 |
| tartronic acid | <0.01 | 0.01 | 0.01 | 0.02 |
| oxalic acid | <0.01 | 0.01 | 0.03 | 0.03 |
| conversion (35'): | 100% | | | |
| selectivity (35'): | 96% | | | |
| activity (35'): | 2,400 g of gluconic acid per g of Pd per h. | | | |

While conversion and selectivity value here too are satisfactory, activity values again are inadequate.

CONTROL TEST 3

The catalyst is prepared as in Example 1 except for only adding a 25% by weight aqueous hexachloroplatinic acid. A Pt/activated charcoal catalyst with 5% by weight Pt is obtained. Glucose oxidation and analysis are as in Example 1. The following values are obtained:

TABLE IV

| Time (minutes) | Amount of material ($10^{-2}$ moles) | | | | |
|---|---|---|---|---|---|
| | 10 | 25 | 40 | 60 | 120 |
| gluconic acid | 1.37 | 2.74 | 3.32 | 4.16 | 4.96 |
| glucaric acid | 0.01 | 0.04 | 0.10 | 0.12 | 0.22 |
| tartaric acid | <0.01 | 0.01 | 0.03 | 0.03 | 0.11 |
| tartronic acid | <0.01 | 0.02 | 0.03 | 0.05 | 0.16 |
| oxalic acid | <0.01 | 0.02 | 0.03 | 0.03 | 0.05 |
| conversion (120'): | 62% | | | | |
| selectivity (120'): | 90% | | | | |
| activity (120'): | 400 g of gluconic acid per g of Pt per h. | | | | |

Conversion, selectivity and activity all are unsatisfactory.

EXAMPLE 2

The catalyst is prepared as in Example 1, except as follows:

A mixture of hexachloroplatinic acid, tetrachloropalladium acid and bismuth solution is added in such an amount to the activated charcoal suspension that a Pt/Pd/Bi-activated charcoal catalyst with 0.1% by weight Pt, 4.9% by weight Pd and 5% by weight Bi is obtained. Glucose oxidation and analysis are as in Example 1. The following values are obtained:

TABLE V

| Time (minutes) | Amount of Material ($10^{-2}$ moles) | | | |
|---|---|---|---|---|
| | 18 | 20 | 22 | 25 |
| glucose | 0.92 | 0.21 | 0.01 | <0.01 |
| gluconic acid | 7.68 | 8.33 | 8.51 | 8.47 |
| fructose | 0.15 | 0.17 | 0.11 | 0.10 |
| glucaric acid | 0.01 | 0.02 | 0.09 | 0.12 |
| tartaric acid | <0.01 | <0.01 | 0.01 | 0.02 |
| tartronic acid | <0.01 | <0.01 | 0.01 | 0.02 |
| oxalic acid | <0.01 | 0.03 | 0.03 | 0.04 |
| conversion (22'): | 100% | | | |
| selectivity (22'): | 97% | | | |
| activity (22'): | 3,800 g of gluconic acid per g of total precious metal per h. | | | |

EXAMPLE 3

The catalyst is prepared as in Example 1 except for the following differences:

A mixture of hexachloroplatinic acid, tetrachloropalladium acid and bismuth solution is added in such amounts to the activated charcoal suspension that a Pt/Pd/Bi-activated charcoal catalyst with 2.5% by weight Pt, 2.5% by weight Pd and 5% by weight Bi is obtained. Glucose oxidation and analysis are as in Example 1.

TABLE VI

| Time (minutes) | Amount of material ($10^{-2}$ moles) 25 |
|---|---|
| glucose | <0.01 |
| gluconic acid | 8.56 |
| fructose | 0.15 |
| glucaric acid | 0.08 |
| tartaric acid | <0.01 |
| tartronic acid | 0.01 |
| oxalic acid | 0.01 |
| conversion (25'): | 100% |
| selectivity (25'): | 97% |
| activity (25'): | 3,400 g of gluconic acid per g of total precious metal per h. |

Repeating the preparation under the same conditions but while carrying out the glucose oxidation at pH 9 gave comparable results.

EXAMPLE 4

The catalyst composition and preparation are as in Example 1. In the glucose oxidation, the reaction temperature is lowered to 30° C. The experiment is carried out and analyzed as described in Example 1. The following values were obtained:

TABLE VII

| Time (minutes) | Amount of material ($10^{-2}$ moles) | | |
|---|---|---|---|
| | 15 | 20 | 25 |
| glucose | 1.80 | 0.48 | <0.01 |
| gluconic acid | 6.83 | 8.13 | 8.55 |
| fructose | 0.10 | 0.14 | 0.19 |
| glucaric acid | 0.01 | 0.01 | 0.02 |
| tartaric acid | <0.01 | <0.01 | <0.01 |
| tartronic acid | <0.01 | <0.01 | <0.01 |
| oxalic acid | <0.01 | <0.01 | <0.01 |
| conversion (25'): | 100% | | |
| selectivity (25'): | 97% | | |
| activity (25'): | 3,400 g of gluconic acid per g of total precious metal per h. | | |

EXAMPLE 5

The catalyst composition and preparation is that of Example 1. The pH value is kept at 7.5 in the glucose oxidation. The experiment is carried out and analyzed as in Example 1. The following values are obtained:

TABLE VIII

| Time (minutes) | Amount of material ($10^{-2}$ moles) | | |
|---|---|---|---|
| | 25 | 30 | 45 |
| glucose | 1.00 | 0.76 | 0.45 |
| gluconic acid | 7.58 | 7.75 | 8.10 |
| fructose | 0.18 | 0.22 | 0.21 |
| glucaric acid | 0.02 | 0.03 | 0.05 |
| tartaric acid | <0.01 | <0.01 | <0.01 |
| tartronic acid | <0.01 | <0.01 | <0.01 |
| oxalic acid | <0.01 | <0.01 | <0.01 |
| conversion (45'): | 95% | | |
| selectivity (45'): | 97% | | |
| activity (45'): | 1,800 g of gluconic acid per g of total precious metal per h. | | |

CONTROL TEST 4

The catalyst is prepared as in Example 1 except that: A mixture of hexachloroplatinic acid and bismuth solution is added in such amounts to the activated charcoal suspension that Pt/Bi-activated charcoal catalyst with 5% by weight Pt and 5% by weight Bi is obtained. The glucose oxidation and the analysis are carried out as in Example 1. The following values are obtained:

TABLE IX

| Time (minutes) | | Amount of material ($10^{-2}$ moles) | | | |
|---|---|---|---|---|---|
| | | 20 | 23 | 25 | 30 |
| glucose | | 0.64 | 0.59 | 0.38 | 0.15 |
| gluconic acid | | 7.90 | 7.91 | 8.10 | 8.33 |
| fructose | | 0.22 | 0.24 | 0.22 | 0.17 |
| glucaric acid | | <0.01 | 0.02 | 0.06 | 0.09 |
| tartaric acid | | <0.01 | <0.01 | ≦0.01 | 0.01 |
| tartronic acid | | <0.01 | <0.01 | ≦0.01 | 0.01 |
| oxalic acid | | <0.01 | <0.01 | ≦0.01 | 0.03 |
| conversion | (30'): | 98% | | | |
| selectivity | (30'): | 96% | | | |
| activity | (20'): | 3,900 g of gluconic acid per g of Pt per h. | | | |
| | (30'): | 2,700 g of glutonic acid per g of Pt per h. | | | |

The catalyst envinces high initial activity. However, the glucose is not completely converted following a reaction time of 30 minutes.

CONTROL TEST 5

The catalyst is prepared as in the Control Test 4, however with half the amount of platinum and bismuth. A Pt/Bi-activated charcoal catalyst with 2.5% by weight Pt and 2.5% by weight Bi is obtained. Glucose oxidation and analysis are carried out as in Example 1. The following values are obtained:

TABLE X

| Time (minutes) | | Amount of material ($10^{-2}$ moles) | | | | |
|---|---|---|---|---|---|---|
| | | 10 | 20 | 30 | 40 | 60 |
| glucose | | 4.45 | 2.60 | 1.80 | 1.00 | 0.95 |
| gluconic acid | | 4.10 | 5.89 | 6.64 | 7.40 | 7.40 |
| fructose | | 0.20 | 0.21 | 0.21 | 0.23 | 0.22 |
| glucaric acid | | 0.01 | 0.03 | 0.06 | 0.07 | 0.10 |
| tartaric acid | | <0.01 | <0.01 | 0.01 | 0.01 | 0.05 |
| tartronic acid | | <0.01 | <0.01 | 0.02 | 0.03 | 0.07 |
| oxalic acid | | <0.01 | <0.01 | <0.01 | 0.03 | 0.01 |
| conversion | (60'): | 89% | | | | |
| selectivity | (60'): | 94% | | | | |
| activity | (40'): | 3,600 g of gluconic acid per g of Pt per h. | | | | |
| | (60'): | 2,400 g of gluconic acid per g of Pt per h. | | | | |

While the catalyst evinces high initial activity, glucose however is converted incompletely.

CONTROL TEST 6

The catalyst is prepared as in the Control Test 4, except that:

A mixture of hexachloroplatinic acid and bismuth solution is added in such quantities to the activated charcoal suspension that a Pt/Bi-activated charcoal catalyst with 5% by weight Pt and 10% by weight Bi is obtained. Glucose oxidation and analysis are carried out as in Example 1. The following values are obtained:

TABLE XI

| Time (minutes) | Amount of material ($10^{-2}$ moles) | | | |
|---|---|---|---|---|
| | 20 | 25 | 35 | 40 |
| glucose | 1.55 | 0.73 | 0.58 | 0.41 |
| gluconic acid | 6.93 | 7.65 | 7.64 | 7.60 |
| fructose | 0.18 | 0.21 | 0.19 | 0.22 |
| glucaric acid | 0.06 | 0.13 | 0.28 | 0.42 |
| tartaric acid | 0.01 | 0.02 | 0.03 | 0.05 |
| tartronic acid | 0.03 | 0.03 | 0.06 | 0.09 |

TABLE XI-continued

| Time (minutes) | Amount of material ($10^{-2}$ moles) | | | |
| --- | --- | --- | --- | --- |
|  | 20 | 25 | 35 | 40 |
| oxalic acid | 0.03 | 0.03 | 0.06 | 0.08 |
| conversion (25'): | 92% | | | |
| selectivity (25'): | 95% | | | |
| activity (25'): | 3,000 g of gluconic acid per g of Pt per h. | | | |

Conversion is unsatisfactory. Glucose is converted incompletely.

Further variations and modifications of the foregoing invention will become apparent to those skilled in the art and are intended to be encompassed by the claims appended hereto.

We claim:

1. A process for preparing gluconic acid or an alkali metal salt thereof comprising:
    carrying out an oxidation reaction by oxidizing glucose with oxygen or with an oxygen containing gas in an aqueous solution in the presence of a catalytic amount of a precious metal component consisting of platinum and palladium supported catalyst containing bismuth and a and at an alkaline pH maintained by continuous addition of an alkali compound until the degree of optimal conversion determined by intermediate analysis has been reached, said catalyst being supported on activated charcoal and being formed by simultaneously depositing on said activated charcoal an active phase consisting of platinum, palladium and bismuth and containing from 0.1 to 10% by weight of the precious metal component containing the platinum and palladium and from 0.01 to 20% by weight of bismuth, the weight ratio of platinum to palladium ranging from 1:99 to 70:30.

2. A process for preparing gluconic acid or an alkali metal salt thereof comprising:
    carrying out an oxidation reaction by oxidizing glucose with oxygen or with an oxygen containing gas in an aqueous solution in the presence of a supported catalyst precious metal component consisting of platinum and palladium containing bismuth and a
    at a reaction temperature from between 20° and 80° C. and at a pH value of 8.0 to 11,
    maintaining said pH by continuous addition of an alkali metal hydroxide,
    carrying out said oxidation reaction until the degree of optimal conversion of glucose as determined by intermediate analysis has been reached,
    the proportion of said catalyst to the glucose being a maximum of 0.2 on a weight basis, said catalyst being supported on activated charcoal and being formed by simultaneously depositing on said activated carbon an active phase consisting of platinum, palladium and bismuth and containing from 0.1 to 10% by weight of the precious metal component containing platinum and the palladium and from 0.01 to 20% by weight of bismuth, the weight ratio of platinum to palladium ranging from 1:99 to 70:30.

3. The process of claim 1 wherein the weight ratio of platinum to palladium is from 15:85 to 50:50.

4. The process of claim 1 wherein the weight ratio of platinum to palladium is from 15:85 to 25:75.

5. The process of claim 1 wherein the reaction is carried out under the oxygen containing gas between standard pressure and 10 bars.

6. The process of claim 1 wherein the reaction is carried out under the oxygen containing gas between standard pressure and 3 bars.

7. The process of claim 1 further comprising carrying out a separation of the catalyst after said reaction.

8. The process of claim 7 further comprising converting the alkali metal gluconate resulting from the reaction into the free acid.

9. The process of claim 1 wherein glucose is used as a 10 to 20% by weight solution.

10. The process of claim 1 wherein the reaction temperature is from 30° to 60° C.

11. The process of claim 1 wherein the pH value of the reaction is 9 to 11.

12. The process of claim 1 wherein pulverulent activated charcoal is used as the catalyst support.

13. The process of claim 1 wherein the weight ratio of catalyst to glucose is less than 0.1.

14. The process of claim 13 wherein the charcoal has a BET surface area of greater than 500 g/m².

15. A process for preparing gluconic acid or an alkali metal salt thereof comprising:
    carrying out an oxidation reaction by oxidizing glucose with oxygen or with an oxygen containing gas in an aqueous solution in the presence of a catalytic amount of a precious metal component consisting of platinum and palladium supported catalyst containing bismuth and a and at an alkaline pH maintained by continuous addition of an alkaline compound until the degree of optimal conversion determined by comparison with a standard has been reached, said catalyst being supported on activated charcoal and being formed by simultaneously depositing on said activated carbon an active phase consisting of platinum, palladium and bismuth, and containing from 0.1 to 10% by weight of the precious metal component containing the platinum and the palladium and from 0.01 to 20% by weight of bismuth.

16. The process of claim 15 wherein the weight ratio of platinum to palladium is 1:99 to 70:30.

17. The process claim 15 wherein the reaction is stopped before undesired byproducts contaminate the reaction.

18. The process according to claim 1 wherein the reaction is carried out under the oxygen containing gas at 3 bars pressure.

* * * * *